(12) United States Patent
Sharma et al.

(10) Patent No.: US 10,689,683 B2
(45) Date of Patent: Jun. 23, 2020

(54) SYSTEMS AND METHODS FOR DETERMINING THE CONCENTRATIONS OF MULTIPLE SPECIES USING MULTIPLE SENSORS

(71) Applicant: ABB Schweiz AG, Baden (CH)

(72) Inventors: Saumya Sharma, Hartford, CT (US); Yixin Liu, New Britain, CT (US); Nolan Nicholas, Granby, CT (US)

(73) Assignee: ABB Schweiz AG, Baden (CH)

( * ) Notice: Subject to any disclaimer, the term of this patent is extended or adjusted under 35 U.S.C. 154(b) by 325 days.

(21) Appl. No.: 15/633,409

(22) Filed: Jun. 26, 2017

(65) Prior Publication Data

US 2018/0371520 A1 Dec. 27, 2018

(51) Int. Cl.
| | |
|---|---|
| *G01N 21/00* | (2006.01) |
| *C12Q 1/06* | (2006.01) |
| *C12Q 1/24* | (2006.01) |
| *C12M 1/34* | (2006.01) |

(52) U.S. Cl.
CPC ............... *C12Q 1/06* (2013.01); *C12M 41/12* (2013.01); *C12M 41/32* (2013.01); *C12M 41/34* (2013.01); *C12M 41/46* (2013.01); *C12Q 1/24* (2013.01)

(58) Field of Classification Search
CPC .................. G01N 27/125; G01N 33/0031
USPC ........................................... 422/82.02, 82.05
See application file for complete search history.

(56) References Cited

U.S. PATENT DOCUMENTS 5,545,300 A * 8/1996 Yun ..................... G01N 27/12
204/424

* cited by examiner

*Primary Examiner* — Natalia Levkovich
(74) *Attorney, Agent, or Firm* — Taft Stettinius & Hollister LLP; J. Bruce Shelkopf

(57) ABSTRACT

A plurality of sensors of the same composition or different compositions are provided on a substrate or in a bundle and are sensitive to a plurality of constituent species in a mixed species medium being measured. The sensors of the same composition may each be maintained at different temperatures. The sensors of different compositions may each be maintained at the same temperature or different temperatures. The intersection of measurement values from the plurality of sensors may be used to determine the actual concentrations of the constituent species (e.g., hydrogen and oxygen) in the mixed species medium.

18 Claims, 8 Drawing Sheets

SYSTEMS AND METHODS FOR DETERMINING THE CONCENTRATIONS OF MULTIPLE SPECIES USING MULTIPLE SENSORS

TECHNICAL FIELD

The present application discloses systems and methods for determining the concentrations of multiple species in a medium using multiple sensors.

BACKGROUND

Sensors are used to measure the concentrations of constituents, such as gas phase constituents, in various samples. In many known implementations of sensors measuring constituent concentrations, however, the measurements are often impacted by other interfering species in the sample. Further, many known implementations utilize a separate sensor to detect each unique species in the medium being measured.

SUMMARY

A sensor array of a plurality of sensors of the same composition is provided. Each sensor of the array of sensors is maintained at a distinct temperature. A readout of each sensor is measured. The actual concentrations of the constituents in the medium are determined by the common measurement values as between each of the sensors held at different temperatures.

A sensor array of a plurality of sensors of different compositions is provided. Each sensor is maintained at the same or different temperatures. A readout of each sensor is measured. The actual concentrations of the constituents in the medium are determined by the common measurement values as between each of the sensors of different compositions held at the same and/or different temperatures.

BRIEF DESCRIPTION OF THE DRAWINGS

In the accompanying drawings, structural embodiments are illustrated that, together with the detailed description provided below, describe exemplary embodiments of a sensor array that can determine the concentration of more than one constituent in a medium having a plurality of constituents without impact from interfering constituents. One of ordinary skill in the art will appreciate that a single component in the drawings and description may be designed as multiple components and that multiple components in the drawings and description may be designed as a single component.

Further, in the accompanying drawings and description that follow, like parts are indicated throughout the drawings and written description with the same reference numerals, respectively. The figures are not drawn to scale and the proportions of certain parts have been exaggerated for convenience of illustration.

DETAILED DESCRIPTION

Figure 1:
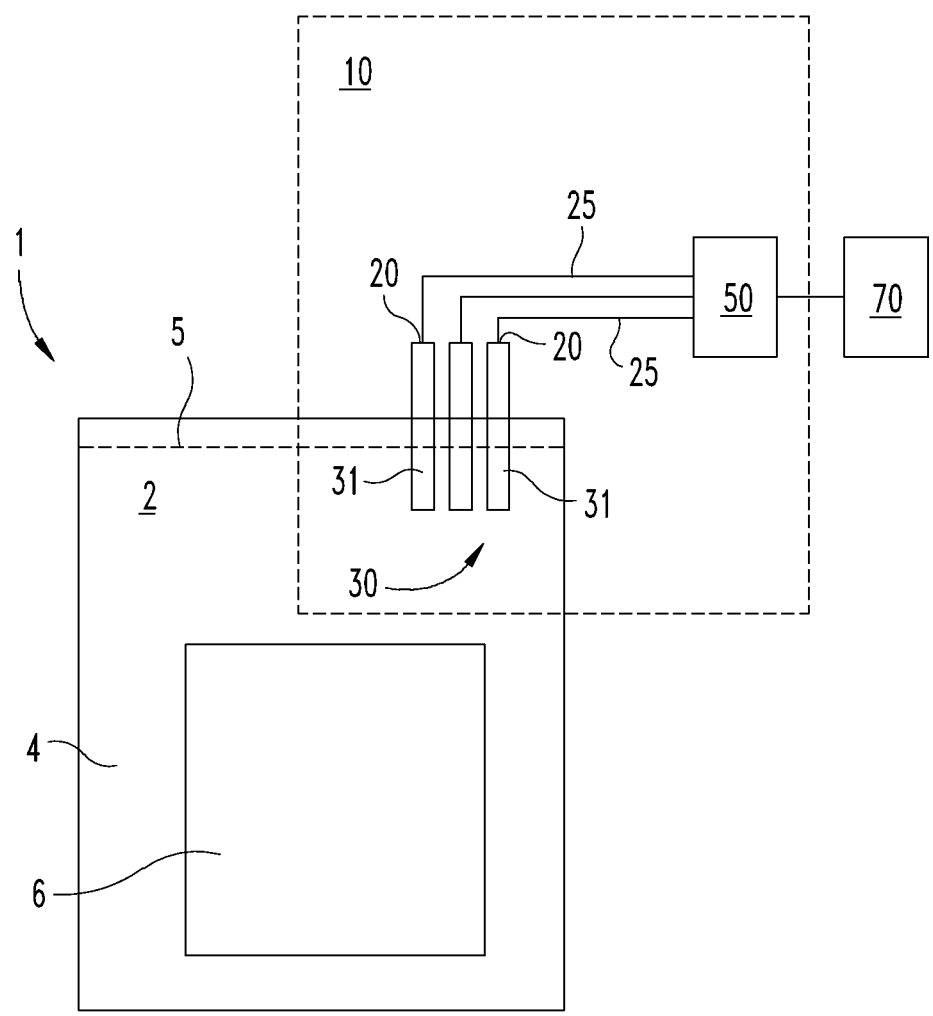
FIG. 1 depicts an illustrative embodiment of a sensor array as arranged to measure constituent concentration in a liquid or gas phase medium, such as insulation fluid of an electrical apparatus.
Figure 2A:
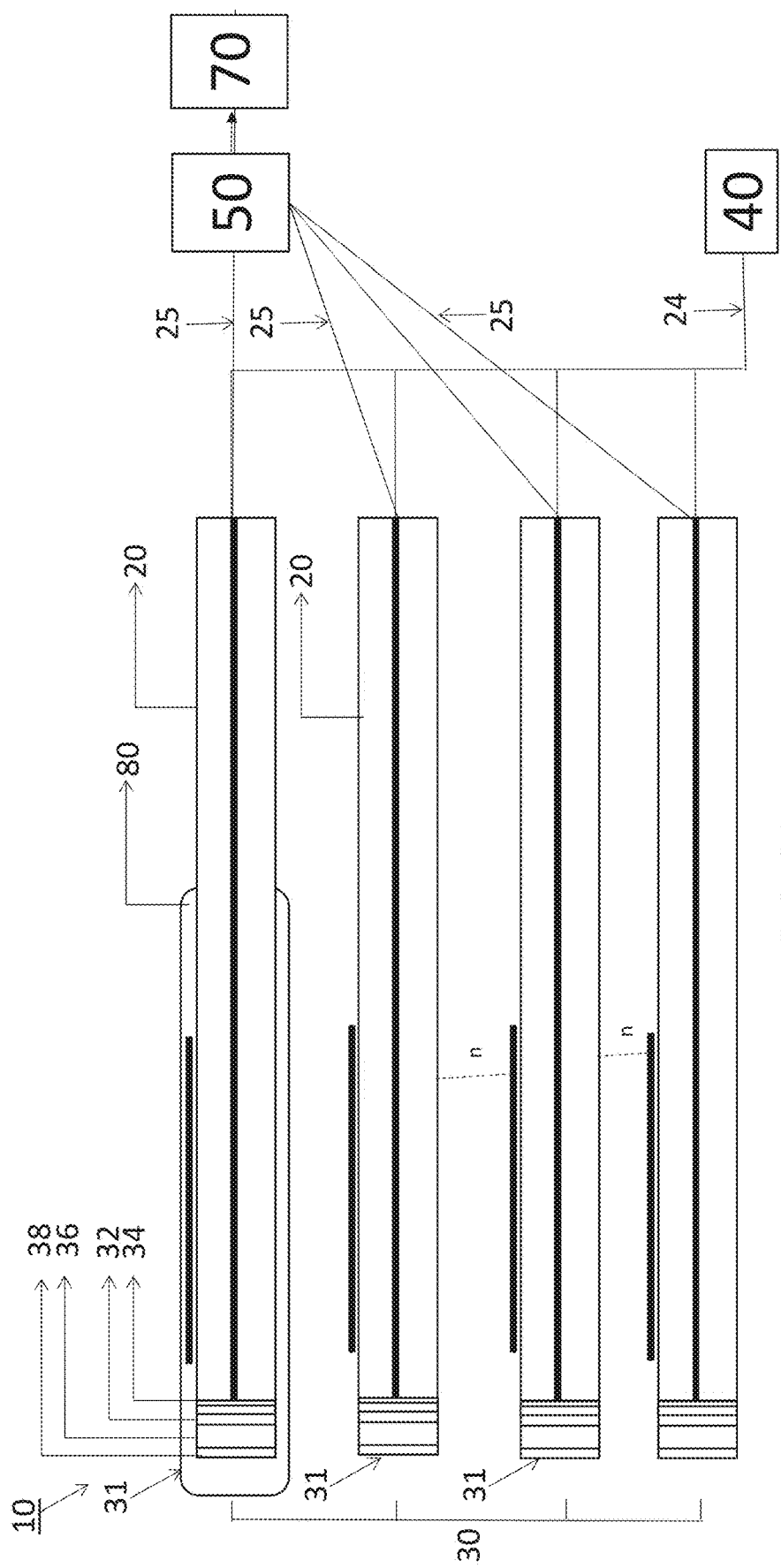
FIG. 2a depicts the sensor array, heating element, output section, processing unit, and light source.
Figure 2B:
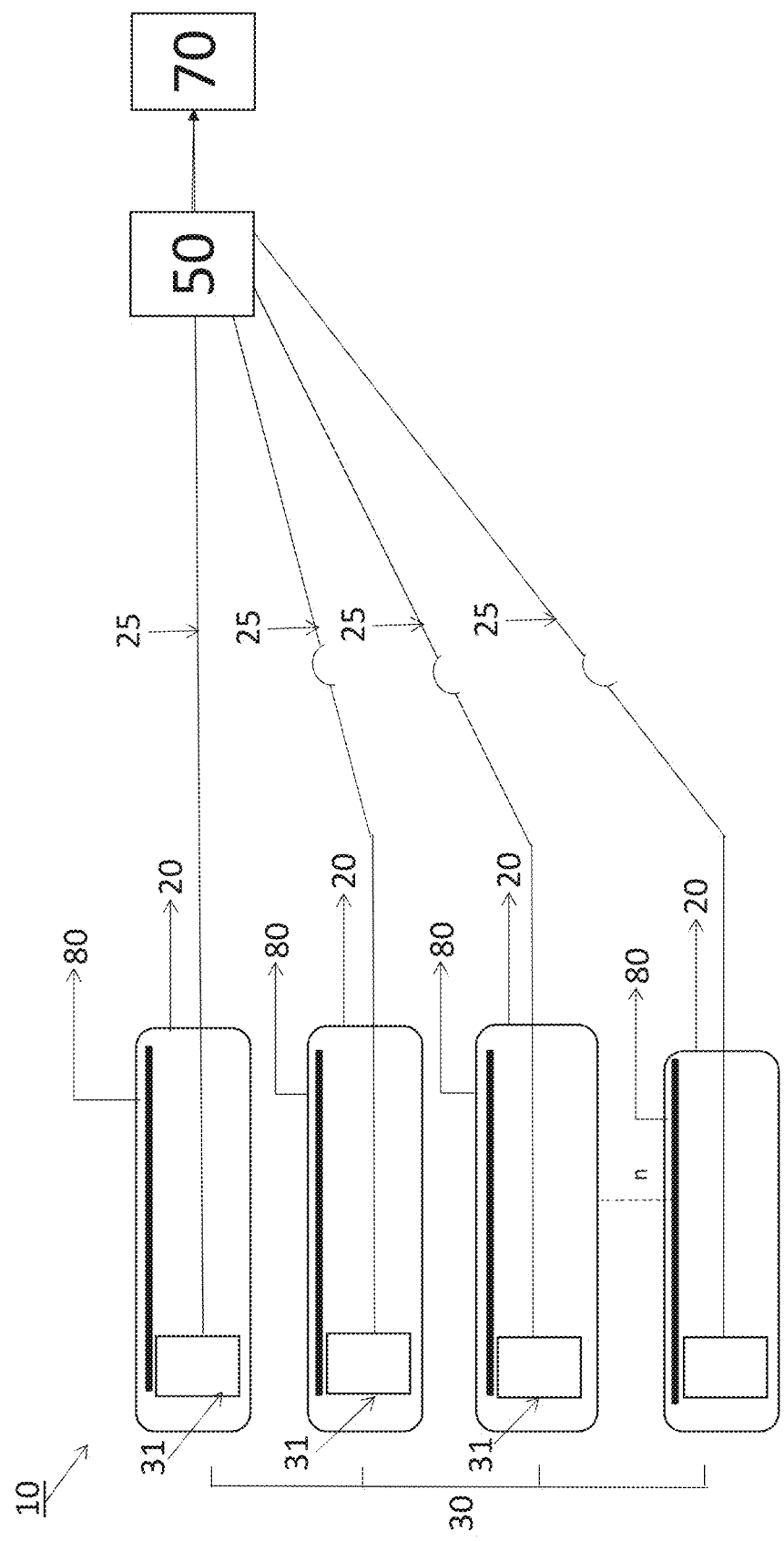
FIG. 2b depicts the sensor array, heating element, output section, and processing unit.

An illustrative embodiment of a sensor array 30, as shown in FIGS. 1, 2a, and 2b, has a plurality of gas sensors 31 of the same composition or of different compositions. The present application contemplates that a plurality of gas sensors having different compositions include: each of the plurality of gas sensors has a composition different than the other sensors; or the plurality of gas sensors includes sensors having at least two different compositions and the different compositions may be by comparison of an individual sensor or a group of sensors of the same composition with the other sensors. Each gas sensor 31 of the sensor array 30 has a layered composition of thin film metal deposited by sputtering targets along with other protective materials arranged in a stack. The sensor array 30 has a plurality of sensors 31 mounted on the same substrate 20 such as a plate, window, lens, casing or tips of a fiber. Alternatively, each sensor 31 of the sensor array 30 may be mounted individually to a separate substrate 20 and bundled together to create the sensor array 30.

The sensor array 30 is in contact with or immersed in the medium to be measured, and the medium is in a liquid or gas phase. Examples of applications in which the sensor array 30 can operate, include but are not limited to measuring concentrations of chemical constituents in a gas stream containing multiple constituents including $H_2$ and $O_2$ and measuring the concentration of dissolved gas in a liquid medium such as hydrogen ($H_2$) present in the medium. When the medium being measured is a liquid, the sensor 31 is placed in contact with the medium and each sensor 31 of the array 30 is brought to and maintained at a specific temperature. Species such as $O_2$, CO, $CO_2$, $CH_4$, $H_2O$, $C_2H_2$, $C_2H_4$, and other constituent species are found or are dissolved in the medium. An example of a medium is transformer insulating fluid such as dielectric fluid. It should be understood that the medium being measured by the sensor array 30 may be an entirely gas phase medium.

When the medium being measured is a gas flowing through a tube, the tube may contain the fiber upon which the sensor 31 is mounted and the sensor 31 is in contact with the inside wall of the tube. Therefore, the sensor 31 is heated to the desired temperature when the tube is heated. In the case of a liquid medium such as dielectric fluid that contains dissolved gas constituents, the sensor fiber element may be in direct contact with a heating element 80 such as a thermocouple and a PID controller (not shown) in a feedback loop that is used to maintain the temperature of the sensor 31. The PID controller feedback loop is used to minimize the temperature increase of the fluid 2 with which the heated sensor 31 is in contact.

With reference to FIG. 1, an exemplary schematic view of a transformer 1 is shown and has a sensor array 30 system 10 for measuring the concentration of dissolved gases in an insulating medium 2. The system 10 has the sensor array 30 provided on a substrate 20, a sensor output section 50, and a processing unit 70 connected to the output section 50.

The transformer 1 has a housing 4 and an active part 6 such as a core and coil windings immersed in the insulating medium 2. The top level 5 of the insulating medium 2 is indicated and there is gas space above the top level 5. While a transformer 1 is provided as a non-limiting example of electrical equipment, other insulation-liquid-filled electrical equipment such as shunt reactors and bushings have mediums that may be measured by the sensor array 30. Alternatively, the sensor array 30 may be operable to measure the concentration of constituents in a gas stream.

With reference to FIG. 2a, each sensor 31 of the sensor array 30 has a composition that is sensitive to a plurality of constituents in the medium and is formed wholly of a metal alloy of any of the compositions described herein. In one embodiment, each sensor 31 has an adhesion layer 34, a constituent sensitive layer 32, a catalytic layer 36, and a protective coating 38. The adhesion layer 34 may be formed of titanium and provided between the constituent sensitive layer 32 and the substrate 20. The constituent sensitive layer 32 is formed of MgTi, MgZrNi or MgTiPd. By way of non-limiting example, the particular stoichiometry of the constituent sensitive layer 32 and/or catalytic layer 36 may be: $Mg_{67}Ti_{33}Mg_{60}Ti_{40}$, $Mg_{73}Ti_{27}$ or $Mg_{55}Zr_{11}Ni_{34}$. The protective coating 38 is formed of $SiO_2$, $Al_2O_3$, or PTFE.

Chemical reactions or absorption/desorption of the gas in the constituent sensitive layer 32 of the sensor array 30 may result in the cross-sensitivity of the sensor array 30, however, the temperature dependent measurements described herein exploit the cross-sensitivity of the plurality of sensors in the sensor array 30 and are used to determine the actual concentrations of the constituents in the medium.

Each sensor 31 of the sensor array 30 has the composition of a metal alloy that is thermodynamically responsive. An exemplary sensor stack is $Mg_{62}Ti_{31}Pd_2$ which is a palladium alloy and has a protective coating 38 which is formed of silicon dioxide, $SiO_2$, to protect the sensor from damage due to corrosive and other materials that may damage the sensor. The protective coating 38 permits only certain constituents to access the constituent sensitive layer 32, so as to dissociate the hydrogen ($H_2$) from molecules into atoms, reducing the $H_2$ oxidation state and allowing the $H_2$ to further access the sensor composition or all layers of the sensor 31 in the case of multiple layers.

As the constituent sensitive layer 32 is sensitive to other constituents but not selective based on particular constituents, a sensor response can be extracted reliably despite other constituents such as $O_2$ being present in the medium that previously would have interfered with the $H_2$ concentration measurement. The cross-sensitivity of the constituent sensitive layer 32 was exploited to determine concentration information of $H_2$ and $O_2$ concurrently using two sensors 31 of the same fabrication at two different temperatures. Each sensor 31 has a heating element 80 which provides temperature control to achieve and maintain the desired temperature of each sensor 31.

Alternatively, each sensor 31 is in thermal communication with a single heating element 80 that produces and controls a temperature gradient between the sensors as shown in FIG. 2b. For example, a single sensor 31 of the sensor array 30 is in direct contact with the heating element 80 but due to the proximity of the sensors 31 to one another, each sensor 31 receives transferred heat from the single sensor 31 of the array 30 that is in contact with the heating element 80. It should be understood that temperature gradient may be controlled at the heating element 80 or by a separate temperature controller, such as a PID controller, depending on the application.

In one embodiment, each sensor 31 is exposed to a light source 40 to generate a reading at the sensor output section 50 as is shown in FIG. 2a. Each sensor communicates with the output section over connection 25 which may be a wired or wireless connection with the output section 50. The light source 40 is in communication with the sensors over light guide 24. In order to detect the concentrations of $H_2$, $O_2$, and other constituents present in the medium with which the sensor array 30 is in contact, the constituent sensitive layer 32 is coupled to a light source 40 for receiving light from the light source 40. The light source 40 may provide radiation in the range from near infrared to far infrared to a microwave wavelength range. The output section 50 of the sensor receives the reflected light from the light source 40.

Alternatively, and according to FIG. 2b, each gas sensor 31 has a resistivity value (ohms/cm$^2$) that is measured at the output section 50 of the sensor and used to determine the concentration values of analytes in the medium. Each sensor 31 is provided with a heating element 80 in thermal communication with the sensors 31 and has individual or common temperature control. The measurements derived from the sensor array of FIG. 2b are electronic or electro-chemical. A light source 40 is not required in a resistivity-type measurement of the gas sensor 31.

In the embodiment utilizing reflectivity measurements generated by the light source 40 acting on the constituent sensitive layer 32 of each gas sensor 31, the measurements exhibit different values when the constituent sensitive layer 32 of the gas sensor 31 in a hydrogenated state is analyzed in comparison to a non-hydrogenated state of the constituent sensitive layer 32. The difference in the optical reflectivity values is expressed in micro-watts as the light bounces off of the constituent sensitive layer 32 and the optical behavior of each gas sensor 31 changes from varying levels of opacity to transparency based on the constituent loading of the constituent sensitive layer 32 as the $H_2$ is dissolved therein. For example, the constituent sensitive layer 32 becomes transparent and is therefore less reflective when it is loaded with hydrogen. The reflectance values of the various sensor 31 compositions are temperature-dependent and vary in relation to the difference in temperature values, thus the sensor 31 electronic readouts are also temperature-dependent.

The optical response of the constituent sensitive layer 32 changes depending on temperature from transparent to opaque depending on the constituent dissolved in the gas sensor composition or particularly in the constituent sensitive layer 32. By way of non-limiting example, the response curve, depending on the material used in the constituent sensitive layer 32, changes based on temperature and pressure of the gas as measured in a gas stream or dissolved in the transformer insulating medium. The thickness of the constituent sensitive layer 32 may interact with various light sources 40 such that as the frequency of the light sources 40 increase, the skin depth must be decreased.

As previously mentioned, the readings from the plurality of sensors are determined by the changes in the constituent sensitive layer 32, such as resistivity (ohms/cm$^2$) detected at the sensor output section 50 or the sensor optical properties when acted upon by a light source 40 as detected at the sensor output section 50. In one embodiment, the light source 40 wavelength is from 350-1300 nanometers. In another embodiment, constituent sensitive layer 32 compositions such as MgTi provide reflectance output values when the light source wavelength is from 350-800 nanometers. The light receiver is sensitive to the light source, and the transmission is filtered to remove noise in order for accurate optical measurement. The spectrum utilizable for the measurement varies at one end from ultraviolet light to the far infrared end of the spectrum, and may include microwaves.

In order to measure a mixture containing n constituent species without interference in an embodiment in which the sensors 31 of the sensor array 30 have the same composition, the number of testing temperatures must be equal to or larger than the number of constituent species (n) present in the medium. At each testing temperature at which each sensor 31 of the sensor array 30 is maintained, a unique response pattern and/or calibration curve is exhibited by the respective sensor 31 to each constituent and the overall composition of the mixture. By way of non-limiting example, when $H_2$ and $O_2$ are present in a sample or medium, measurements of the sensor array 30 having at least two sensors of the same composition and each operating at different temperatures were found to provide the exact concentration of $H_2$ and $O_2$ present in the mixed constituent medium at the point of overlap of sensor readout values. Pressure and flow rates of the gas or liquid mediums were not found to meaningfully impact the sensor measurements.

Figure 3A:
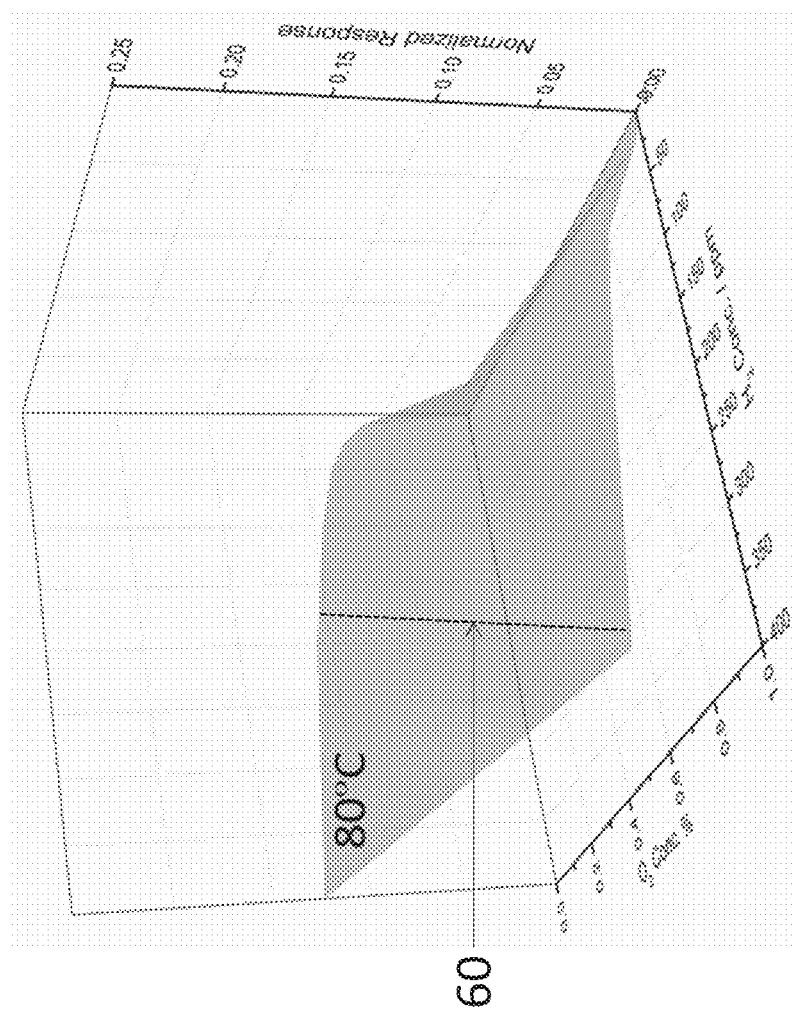
FIG. 3a depicts an exemplary response curve of a first sensor of the sensor array when the sensor is held at 80 degrees Celsius and placed in contact with a mixed species medium.
Figure 3B:
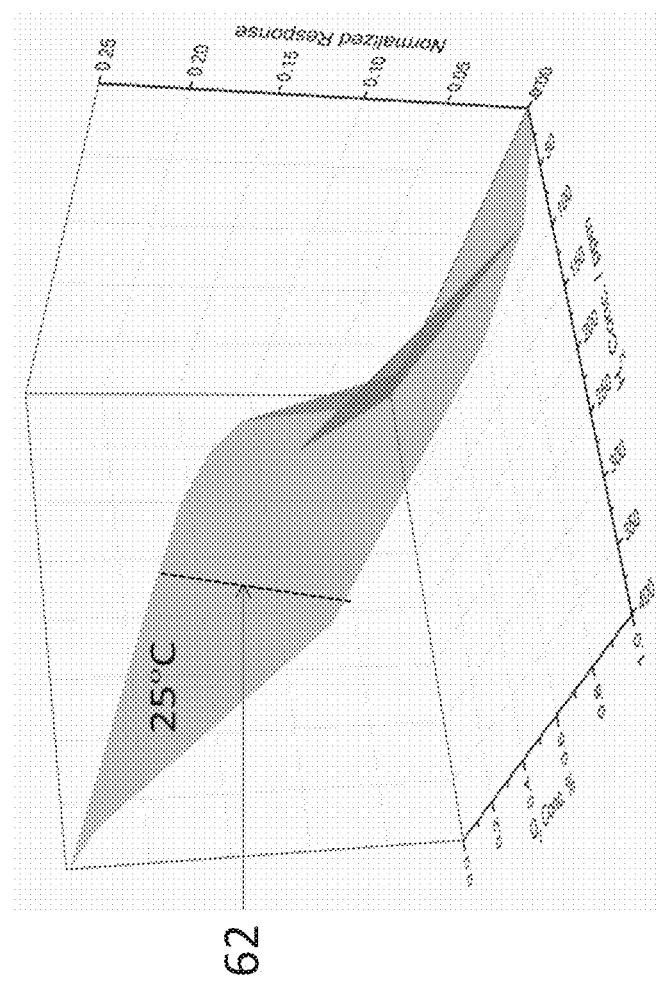
FIG. 3b depicts an exemplary response curve of a second sensor of the sensor array when maintained at 25 degrees Celsius and in contact with the mixed species medium.
Figure 4:
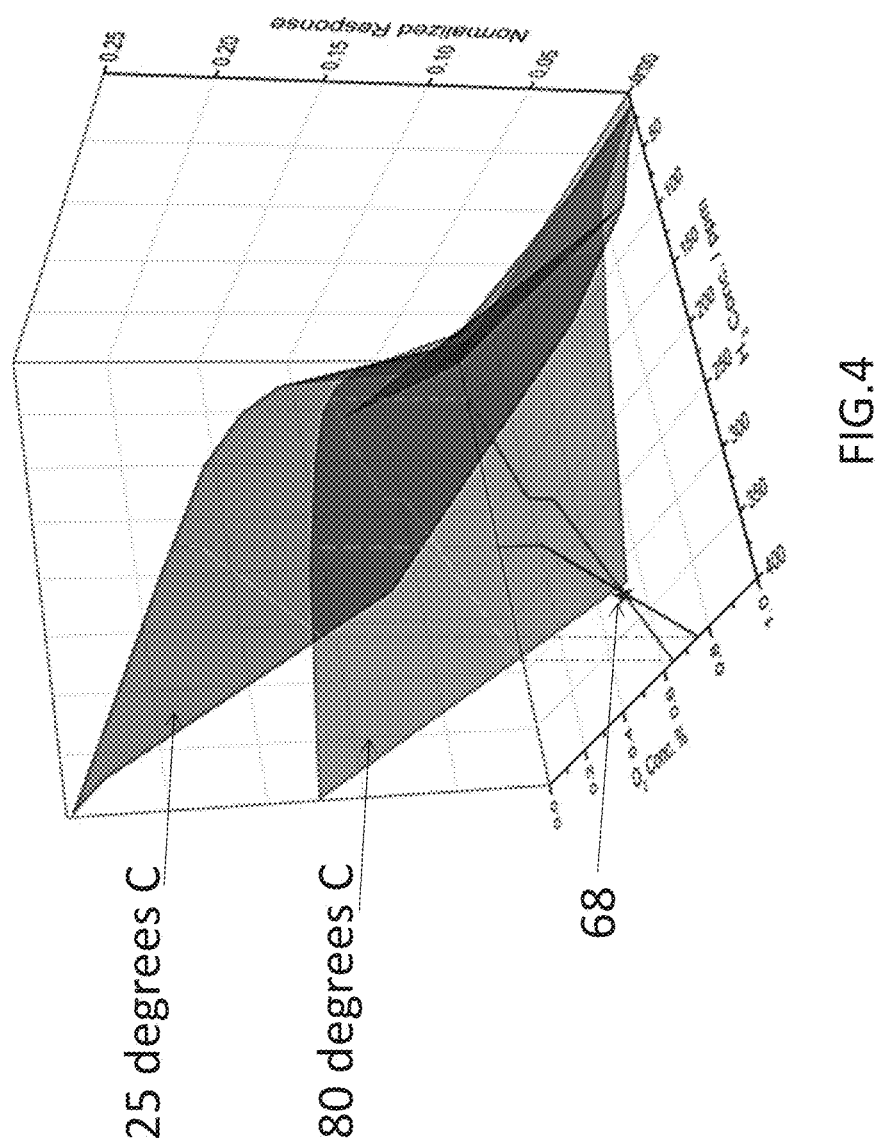
FIG. 4 depicts the superimposition of the sensor response curves of FIGS. 3a and 3b in the mixed species medium on a common chart to determine the convergence point of the possible combinations of constituent concentrations and, thereby, the actual concentration value of each constituent.

With reference to FIG. 3a, a first gas sensor 31 of the sensor array 30 exhibited a response to $H_2$ in a sample and the response was found to be impacted by the presence of $O_2$. In this case, it was not possible to identify the $H_2$ concentration in the presence of an unknown $O_2$ concentration in a medium using a single reading or multiple readings 60 of the sensor that measured 0.1 microwatts at 80 degrees Celsius. Likewise, it was not possible to determine the exact concentrations of $H_2$ and $O_2$ using measurements 62 of the second sensor maintained at 25 degrees Celsius as shown in FIG. 3b. However, when first and second sensors 31 of the sensor array 30 were used to measure the medium and the sensors 31 were maintained at different temperatures of 80 degrees Celsius and 25 degrees Celsius, respectively, as shown in FIGS. 3a and 3b, the result was that the concentrations of $H_2$ and $O_2$ could both be detected at the point where the measurements of the two sensors intersect 68 or overlap, as shown in FIG. 4. It should be understood that temperature differences of at least one degree Celsius as between the sensors 31 in the array 30, provides the sensitivity required to determine the actual concentration of the constituents in the medium at the point of intersection 68. It should be understood that certain applications may require additional sensors of the same composition in order to determine the concentration of the plurality constituents when the temperature difference at which the plurality of sensors are maintained is small.

Figure 3D:
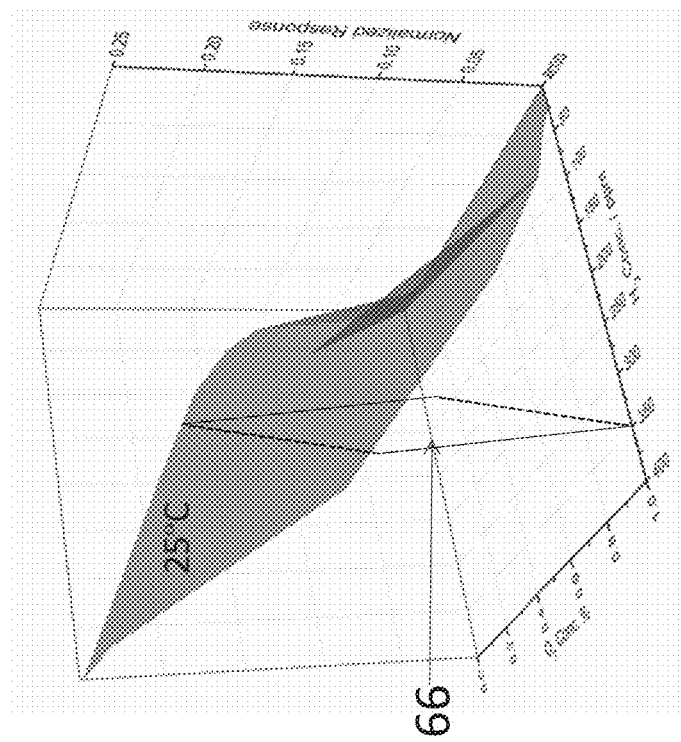
FIG. 3d depicts the sensor response curve of FIG. 3b and the possible combinations of constituent concentrations present in the mixed species medium on the xy plane.
Figure 3C:
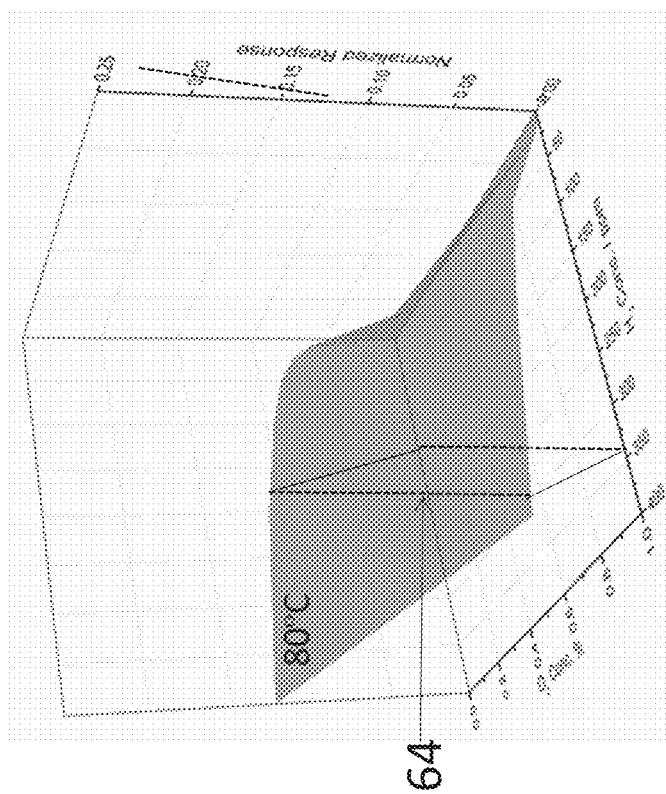
FIG. 3c depicts the sensor response curve of FIG. 3a and the possible combinations of constituent concentrations present in the mixed species medium on the xy plane.

FIGS. 3c and 3d show the possible combinations of $H_2$ and $O_2$ concentrations that lead to the normalized sensor output readings of 0.10 at 80 degrees Celsius and 0.15 at 25 degrees Celsius, respectively. The X-axis represents $O_2$ concentration percentage, the Y-axis represents $H_2$ concentration in parts per million, and the Z-axis is the normalized response of the sensor.

With particular reference to FIG. 3c, the response values of the first sensor 31 at 80 degrees Celsius with measurements of varying concentrations of $H_2$ and varying concentrations of $O_2$ present in the medium are shown as they intercept on the xy-plane 64. With reference to FIG. 3d, the response values of the second sensor 31 at 25 degrees Celsius with measurements of varying concentrations of $H_2$ and varying concentrations of $O_2$ present in the medium are shown as they intercept on the xy-plane 66.

FIG. 4 depicts the superimposed response curves of FIGS. 3a and 3b, or alternatively, FIGS. 3c and 3d. The data is analyzed by a processing unit 70 which has a processor and internal memory to determine all possible $H_2$ and $O_2$ concentration measurements that provide the same readout values at the output section 50 for the plurality of sensors operated each at different temperatures. Intersection point 68 indicated in FIG. 4 provides the $H_2$ and $O_2$ concentrations resulting in the same readout value from the plurality of sensor measurement values when the sensors are maintained at 25 degrees Celsius and 80 degrees Celsius, respectively. Therefore, the intersection point 68 of the response curves of FIGS. 3a and 3b provide the actual concentrations of $H_2$ and $O_2$ in the sample as 0.55 percent $O_2$ and 325 parts per million Hz, respectively. It should be understood that a third sensor 31 of the same composition in the sensor array 30 may be maintained at a third temperature and provide a third constituent concentration value based upon the intersection point 68 of concentration values as measured by the first, second and third sensors of the sensor array 30. It will be appreciated that the foregoing system and method can be expanded to determine concentrations of any number (n) of constituents using a sensor array 30 comprising at least n sensors 31.

In one embodiment, the sensor array 30 has a plurality of gas sensors having the same constituent sensitive layer 32 of MgTi, MgZrNi or MgTiPd with exemplary stoichiometry that includes but is not limited to: $Mg_{67}Ti_{33}$, $Mg_{60}Ti_{40}$, $Mg_{73}Ti_{27}$ or $Mg_{55}Zr_{11}Ni_{34}$ duplicated as between the constituent sensitive layers 32 of the plurality of gas sensors in the sensor array 30. For example, constituent sensitive layers 32 such as MgTi are sensitive to $H_2$ in an inert background such as $N_2$, however, the response of the optical sensing layer decreases dramatically when $O_2$ is present in the medium or environment being measured.

In one embodiment, the plurality of sensors in the sensor array 30 each have different constituent sensitive layer 32 compositions for detecting $H_2$ and $O_2$ concentrations in a multi-component medium. Typically, chemical reactions or absorption/desorption of the gas in the constituent sensitive layer 32 of the sensor array 30 results in the cross-sensitivity of the sensor array 30. However, this sensitivity is exploited herein by employing sensors 31 having different compositions.

Each sensor of the sensor array 30 formed of sensors 31 having different compositions is operated at the same or different temperatures. The concentration of the plurality of constituents within the presence of interfering constituents is determined using a plurality of sensors having constituent sensitive layers 32 targeting the same constituents. Each sensing element has a unique sensing signature for different mediums rather than a proportional change response signature wherein the mediums are completely gaseous or involve gas dissolved in a liquid medium 2. It should be understood that the temperature difference for achieving readouts from the sensors 31 of the sensor array 30 may be as small as one degree Celsius in some applications that utilize sensors 31 of different compositions maintained at different temperatures.

By way of non-limiting example, the sensor array 30 has a plurality of gas sensors having different constituent sensitive layers 32 as between each sensor. Exemplary metal alloys for this embodiment include but are not limited to: MgTi, MgZrNi, and MgTiPd. Particular stoichiometric values such as $Mg_{67}Ti_{33}$ $Mg_{60}Ti_{40}$, $Mg_{73}Ti_{27}$ or $Mg_{55}Zr_{11}Ni_{34}$ may be used in the constituent sensitive layers 32 of the plurality of gas sensors in the sensor array 30 having different compositions.

It should be understood that constituent sensitive layers 32 such as MgTi are sensitive to $H_2$ in an inert background such as $N_2$, however, the response of the constituent sensitive layer 32 decreases dramatically when $O_2$ is present in the medium or environment being measured.

Figures 5A, 5B:
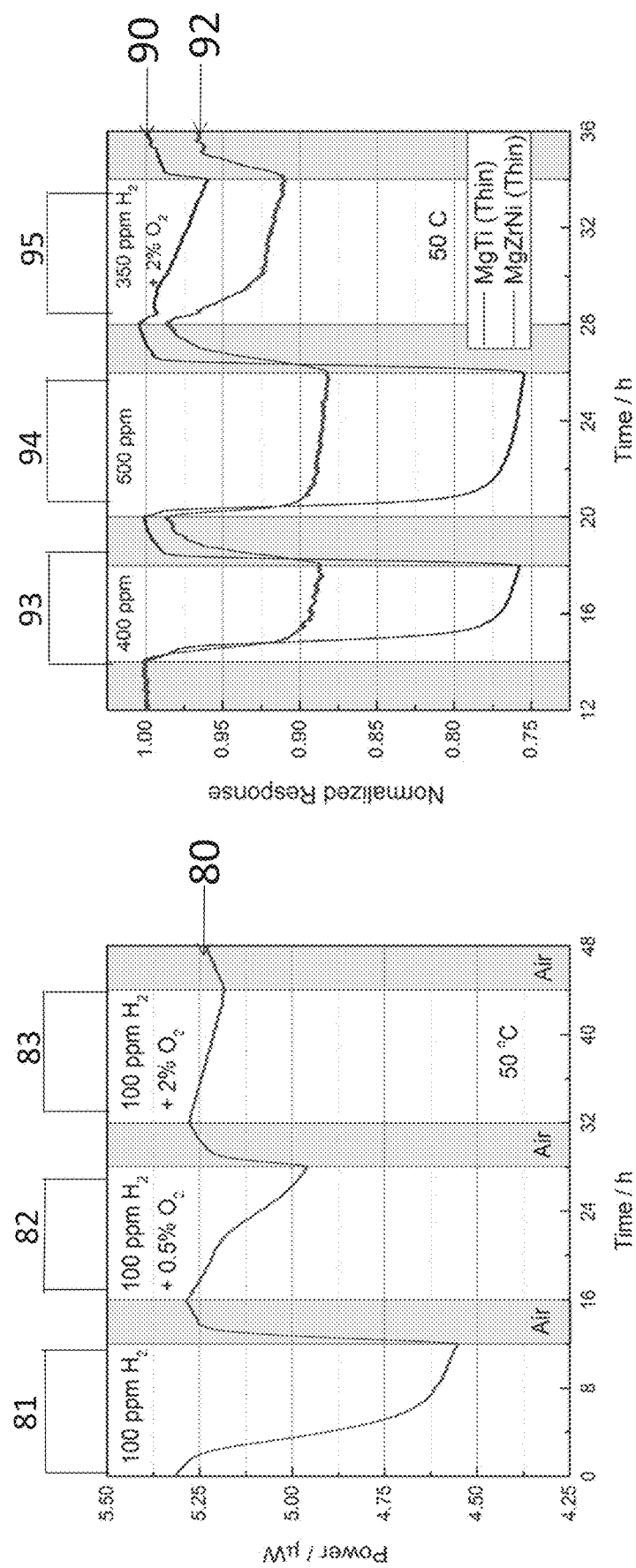
FIG. 5a depicts an exemplary sensor response in relation to a medium having hydrogen, oxygen, and nitrogen constituents.
FIG. 5b depicts an exemplary sensor response of sensors having different compositions in the presence of a medium having hydrogen, oxygen, and nitrogen constituents.

With reference to FIG. 5a, gas phase sensing of a medium over a period of hours is shown. The medium contained 300 ppm $H_2$ as shown by line 81, 300 ppm $H_2$ with 0.5% $O_2$ as shown by line 82 and 300 ppm with 2% $O_2$ as shown by line 83. Gas phase sensing of the medium was conducted at 50 degrees Celsius using the sensor array 30 wherein each of the plurality of sensors 31 had different sensor compositions. The presence of $O_2$ was shown to have a significant impact on $H_2$ sensing results in FIG. 5a. However, it was not possible to determine the $H_2$ concentration impact on the measurement results when the concentration of was $O_2$ unknown.

The accurate detection of $O_2$ in this situation in previously known gas sensors involved a separate $O_2$ sensor for measuring the $O_2$ level independently. A separate $H_2$ sensor was then calibrated to a larger set of $O_2$ levels or the $H_2$ sensor was interrogated at multiple temperatures to differentiate the impact of other constituents on the signal output.

In contrast, the present disclosure employs a sensor array 30 having sensors 31 that target the same constituents, including but not limited to hydrogen, oxygen, and carbon monoxide, by way of example. The constituent sensitive layer 32 composition is a contributing factor to the detection of each species. The result is a unique sensing profile with respect to the various constituents present in the medium such as inert gases or interfering constituents. By combining and analyzing the datasets from each constituent sensitive layer 32 in the sensor array 30, the concentration of the constituents of interest can be determined using a similar method to that described above.

In one embodiment, two different hydrogen sensing element compositions, $Mg_{67}Ti_{33}$ and $Mg_{55}Zr_{11}Ni_{34}$, were tested together at 50 degrees Celsius as depicted in FIG. 5b where line 90 is the MgTi layer response curve and line 92 is the MgZrNi response curve when those compositions are used for constituent sensing in a mixed constituent medium containing varying levels of $H_2$ and $O_2$ over time. While MgTi shows a more sensitive response to 500 ppm nitrogen with the addition of 2% $O_2$ in the gas background, MgZrNi shows better $O_2$ anti-interfering capability as shown in sections 93, 94, and 95 of the graph of FIG. 5b. By analyzing readings from both sensing elements, $H_2$ concentration can be detected and differentiated despite changes in the overall environmental composition.

Various types of constituent sensitive layer 32 compositions may be utilized, but at least two different compositions are used concurrently as between the plurality of gas sensors in the gas sensor array 30 to achieve the results of FIG. 5b. This arrangement provides a more detailed and robust signal in an environment where at least one interfering constituent is present. The different compositions as between the sensors of the plurality of sensors may include a different stoichiometry of the same elemental system such as $Mg_{67}Ti_{33}$ and $Mg_{60}Ti_{40}$ and $Mg_{73}Ti_{27}$. In one embodiment, the differences in composition in each sensor of the plurality of sensors may include different materials systems such as MgTi, MgZrNi, or $Mg_{62}Ti_{31}Pd_7$. Sensor compositions of MgTi, MgZrNi, and MgTiPd are well-suited to transduce chemical signals via optical read-out using the reflectance change measurements previously mentioned for the plurality of sensors in an array of the same composition.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application illustrates various embodiments, and while these embodiments have been described in some detail, it is not the intention of the applicant to restrict or in any way limit the scope of the appended claims to such detail. Additional advantages and modifications will readily appear to those skilled in the art. Therefore, the invention, in its broader aspects, is not limited to the specific details, the representative embodiments, and illustrative examples shown and described. Accordingly, departures may be made from such details without departing from the spirit or scope of the applicant's general inventive concept.

What is claimed is:

1. A system for determining concentrations of a plurality of constituents in a medium, comprising:
    a plurality of sensors in contact with the medium, each sensor of the plurality of sensors having a composition that is sensitive to the plurality of constituents in the medium;
    one or more heating elements in thermal communication with the plurality of sensors; and
    a processing unit configured to control the one or more heating elements to maintain each sensor of the plurality of sensors at a different temperature from the other sensors, the processing unit further configured to receive from each sensor of the plurality of sensors a readout corresponding to a temperature-dependent measurement of the sensor in the medium and compare the plurality of sensor readouts to a set of calibration readouts for the plurality of sensors maintained at the different temperatures to determine actual concentrations of the plurality of constituents in the medium from a point of overlap of concentration values corresponding to the set of calibration readouts and the plurality of sensor readouts, each at the different temperatures.

2. The system of claim 1, wherein the composition of each of the plurality of sensors is provided on a constituent sensitive layer of the corresponding sensor, and wherein the readouts from the plurality of sensors is different for a medium having interfering constituents than for a medium not having interfering constituents.

3. The system of claim 2 wherein the temperature-dependent measurement from each of the plurality of sensors is derived from a group of measurement types consisting of: optical, electronic, and electro-chemical.

4. The system of claim 1 wherein each of the plurality of sensors are of the same composition.

5. The system of claim 1 wherein each of the plurality of sensors are of a different composition.

6. The system of claim 1 wherein the plurality of sensors are mounted on a substrate.

7. The system of claim 1 wherein the plurality of sensors are provided as a bundle.

8. A system for determining concentrations of a plurality of constituents in a medium, comprising:
a plurality of sensors in contact with the medium, each sensor of the plurality of sensors having a different composition that has a unique response to each of the plurality of constituents in the medium;
one or more heating elements in thermal communication with the plurality of sensors; and
a processing unit configured to control the one or more heating elements to maintain each sensor of the plurality of sensors at the measurement temperature, the processing unit further configured to receive from each sensor of the plurality of sensors a readout corresponding to a temperature-dependent measurement of the sensor in the medium and compare the plurality of sensor readouts to a set of calibration readouts for the plurality of sensors maintained at the measurement temperature to determine actual concentrations of the plurality of constituents in the medium from a point of overlap of concentration values corresponding to the set of calibration readouts and the plurality of sensor readouts, each at the measurement temperature.

9. The system of claim 8, wherein for each sensor, the different composition thereof is provided on a constituent sensitive layer, and wherein the readouts from measuring a medium having interfering species are different from the readouts measuring a medium absent from interfering species.

10. The system of claim 9 wherein the temperature-dependent measurement from each sensor is derived from a group of measurement types consisting of: optical, electronic, and electro-chemical.

11. The system of claim 8 wherein the processing unit is configured to control the one or more heating elements so that the measurement temperature for each sensor is different.

12. The system of claim 8 wherein the processing unit is configured to control the one or more heating elements so that the measurement temperature for each sensor is the same.

13. The system of claim 8 wherein the composition for each of the sensors is provided on a constituent sensitive layer of the sensor.

14. The system of claim 13, wherein the different compositions include metal alloys comprising one or more of MgTi, MgZrNi, and MgTiPd.

15. The system of claim 8 wherein the composition has a unique response to each of hydrogen, oxygen, and carbon monoxide.

16. The system of claim 1 wherein the composition of each of the sensors is provided on a constituent sensitive layer and the composition of each of the sensors is different.

17. The system of claim 16, wherein the different compositions include metal alloys comprising one or more of MgTi, MgZrNi, and MgTiPd.

18. The system of claim 1 wherein the composition is sensitive to hydrogen, oxygen, and carbon monoxide.

* * * * *